US009616287B2

(12) United States Patent
Christoforou et al.

(10) Patent No.: US 9,616,287 B2
(45) Date of Patent: Apr. 11, 2017

(54) HAND THERAPY KIT

(71) Applicant: ISOS Solutions, LLC, New Hampton, NY (US)

(72) Inventors: Dimitrios Christoforou, Middletown, NY (US); Vipul Patel, Middletown, NY (US)

(*) Notice: Subject to any disclaimer, the term of this patent is extended or adjusted under 35 U.S.C. 154(b) by 96 days.

(21) Appl. No.: 14/640,943

(22) Filed: Mar. 6, 2015

(65) Prior Publication Data
US 2016/0256738 A1    Sep. 8, 2016

(51) Int. Cl.
| A63B 23/16 | (2006.01) |
| A63B 21/00 | (2006.01) |
| A63B 21/04 | (2006.01) |
| A63B 21/055 | (2006.01) |
| A61F 13/10 | (2006.01) |
| A61F 7/00 | (2006.01) |
| A61F 17/00 | (2006.01) |

(52) U.S. Cl.
CPC ............ *A63B 23/16* (2013.01); *A61F 7/0053* (2013.01); *A61F 13/105* (2013.01); *A61F 17/00* (2013.01); *A63B 21/00189* (2013.01); *A63B 21/0414* (2013.01); *A63B 21/0552* (2013.01); *A61F 2007/0036* (2013.01)

(58) Field of Classification Search
USPC ..................................................... 482/1–148
See application file for complete search history.

(56) References Cited

U.S. PATENT DOCUMENTS

| 4,844,478 | A | * | 7/1989 | Kessler | ................... | A63B 41/00 |
| | | | | | | 473/474 |
| 5,350,304 | A | * | 9/1994 | Fula | ....................... | G09B 19/00 |
| | | | | | | 312/213 |
| 6,918,490 | B1 | * | 7/2005 | Napolitano | ............... | A43C 9/00 |
| | | | | | | 206/227 |
| 7,618,349 | B1 | * | 11/2009 | Muderick | ............ | A63B 21/028 |
| | | | | | | 482/44 |
| 8,157,709 | B2 | * | 4/2012 | Wilkinson | ....... | A63B 21/00069 |
| | | | | | | 482/108 |
| 2006/0094573 | A1 | * | 5/2006 | Weck | .................. | A63B 21/0004 |
| | | | | | | 482/126 |
| 2007/0060448 | A1 | * | 3/2007 | Silagy | ................ | A63B 21/0004 |
| | | | | | | 482/49 |

* cited by examiner

*Primary Examiner* — Stephen Crow
(74) *Attorney, Agent, or Firm* — Intrinsic Law Corp.; Ibrahim M. Hallaj (57) ABSTRACT

A hand therapy kit includes a housing having a lid that is expandable from a folded position to an unfolded position to expose a working surface on an inside of the lid. An elastic cord is attached at two or more anchor points on the working surface to define at least one gap for receiving a finger. The finger can be therapeutically exercised by moving from a first position proximal to the working surface to a second position distal to the working surface. The hand therapy kit can also include removable hand therapy modules.

22 Claims, 7 Drawing Sheets

HAND THERAPY KIT

TECHNICAL FIELD

The present application is directed to systems for therapeutically treating the hand of a patient. In particular, the present application is directed to a multi-part kit integrated into a case, housing or enclosure adapted for providing physical therapy for a hand in a home setting with little or no active participation by a professional therapist during its use.

BACKGROUND

Currently, a patient that needs physical therapy for her hand needs to go to a professional office, such as a doctor's office or a physical therapist's office, to receive treatment. This can be a significant undertaking for a patient that needs to travel a long distance, take time away from work, and/or secure childcare so that she can attend a physical therapy appointment at a professional office. This undertaking is compounded by the number of sessions the patient needs to attend, which can often repeat over multiple weeks or months.

In addition, patients are often frustrated because many of the exercises that they perform with a professional physical therapist could be done at home at a more convenient time and without unnecessary travel. Indeed, some exercises only require the use of common household objects such as rubber bands or clothespins. What is needed is a kit that contains therapeutic objects for home-based physical therapy of the hand.

SUMMARY

The present disclosure is directed to a device and a kit for home-based physical therapy of the hand. The present devices and systems overcome many of the shortcomings of existing devices and systems for treating the hand. In an aspect, the present device can improve strength and/or range of motion of the hand including the fingers thereof. The device and kit include an elastic cord attached to a rigid surface at two or more contact points to define a gap for receiving a finger. A finger can be inserted in the gap and moved form a first position proximal to the rigid surface to a second position distal to the rigid surface for a therapeutic exercise.

IN THE DRAWINGS

For a fuller understanding of the nature and advantages of the present concepts, reference is made to the following detailed description of preferred embodiments and in connection with the accompanying drawings, in which.

DETAILED DESCRIPTION

A hand therapy kit includes a housing having a lid that is expandable from a folded position to an unfolded position to expose a working surface on an inside of the lid. An elastic cord is attached at two or more anchor points on the working surface to define at least one gap for receiving a finger. The finger can be therapeutically exercised by moving from a first position proximal to the working surface to a second position distal to the working surface. The hand therapy kit can also include removable hand therapy modules.

In another aspect, an apparatus for providing home-based physical therapy to a hand is disclosed. The apparatus includes an elastic cord attached to a rigid platform at two or more contact points. The contact points define a gap therebetween for receiving a finger. The finger can be therapeutically exercised by moving from a first position proximal to the rigid platform to a second position distal to the rigid platform.

The hand therapy kit and apparatus can be used by patients to provide physical therapy in a home environment. This provides a more convenient and cost-effective solution for the patient. By using the hand therapy kit and apparatus, the patient can improve strength, dexterity, and/or range of motion of his hand and fingers. Also, use of the kit can reduce healthcare costs and individual patient costs by allowing the user to participate in physical therapy at home with minimal to no involvement by medical personnel (e.g., doctors, physical therapists, etc.) and minimal to no use of medical offices.

The kit can include a camera and a processor for motion recognition. The motion recognition system can include instructions to compare the user's exercise techniques with model exercise techniques to provide feedback to the user. In addition or in the alternative, the kit can include equipment for video calls, such as a display, a processor, a video camera, and a network interface. The user can make video calls with a healthcare provider for instruction, monitoring of the user's progress, and/or health appointments. In addition or in the alternative, the video camera can record the user's exercises for therapists and doctors to use to treat the user and/or research purposes.

Figure 1:
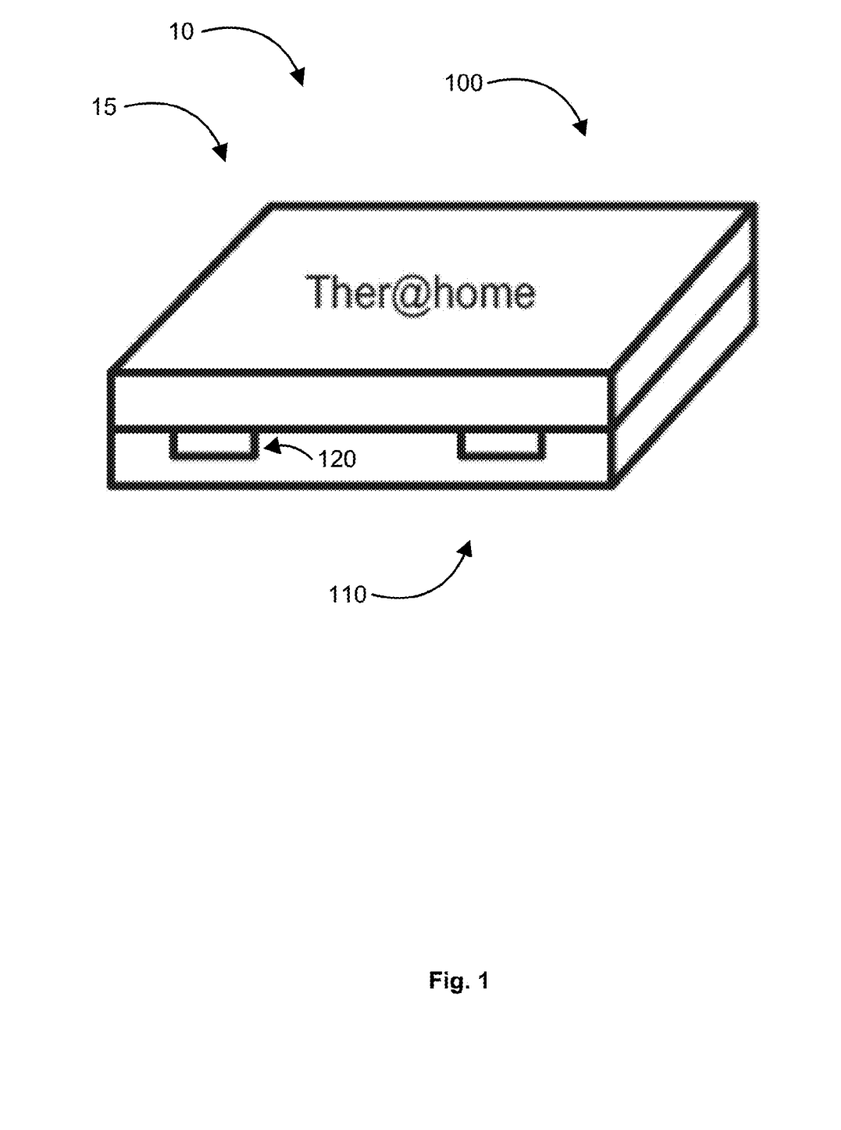
FIG. 1 illustrates a perspective view of a kit according to an embodiment.

FIG. 1 illustrates a perspective view of a kit 10 according to an embodiment. The kit 10 includes various components for therapeutic treatment of the hand as described herein. The kit 10 has an upper lid 100 and a lower lid 110. The upper lid 100 and the lower lid 110 can be connected by a hinge or similar mechanism. Alternatively, the upper lid 100 and lower lid 110 can be disconnected such that the upper lid 100 can be separated from the lower lid 110, for example to use as a work surface as described below. The upper lid 100 and lower lid 110 can be secured shut with an optional latch 120.

Figure 2:
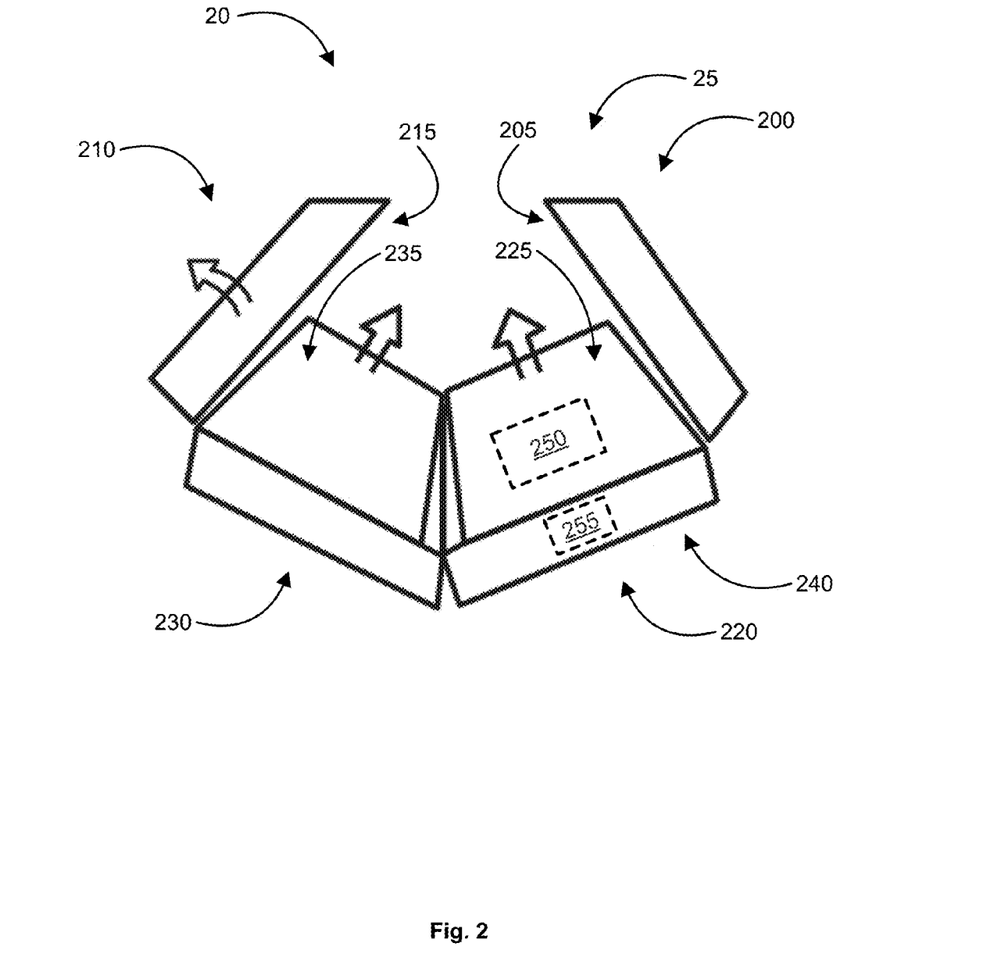
FIG. 2 illustrates a perspective view of a kit according to an embodiment.

FIG. 2 illustrates a perspective view of a kit 20 according to an embodiment. The kit 20 includes an upper lid 200 and a lower lid 210 as previously discussed. The upper lid 200 and lower lid 210 fold out laterally (e.g., in the direction of the arrows illustrated in FIG. 2) to expose secondary lid portions 220, 230, which include working surfaces 225, 235, respectively. The working surfaces 225 and/or 235 can include one or more devices, modules, and/or equipment for therapeutically treating the hand. In some embodiments, a lower surface 205 of the upper lid 200 and/or a lower surface 215 of the lower lid 210 include one or more devices, modules, and/or equipment for therapeutically treating the hand. In addition or in the alternative, the lower surface 205 of the upper lid 200 and/or the lower surface 215 of the lower lid 210 includes a working surface as described above. The working surfaces 225 and/or 235 can include a cavity to receive one or more modules.

In some embodiments, an optional heating element 250 is integrated into the upper lid 200 and/or lower lid 210, for example on one of the working surfaces 225, 235 or on one of the lower surfaces 205, 215. The element 250 can be used to warm paraffin wax (e.g., from the paraffin wax module 530C described below). The heating element 250 can be powered by a battery stored in the kit 20 or by external AC power provided through an electric cord 255, which can be integrated into the kit 20. In an embodiment, the housing or case of the kit can include an integrated AC power plug or connector so that the kit can accept an ordinary AC power extension cord to provide heating or other power to the units within the kit, e.g., as described below. For example the electric cord 255 can pass through the inside of the kit 20 and out through a sidewall 240 of the kit 20. The electric cord 255 can be retractable so that it can be stored inside the kit 20. In some embodiments, the heating element 250 is disposed on a surface below the working surface 225, 235 in which case the working surface 225, 235 is removable so that a user can access the heating element 250.

Figure 3:
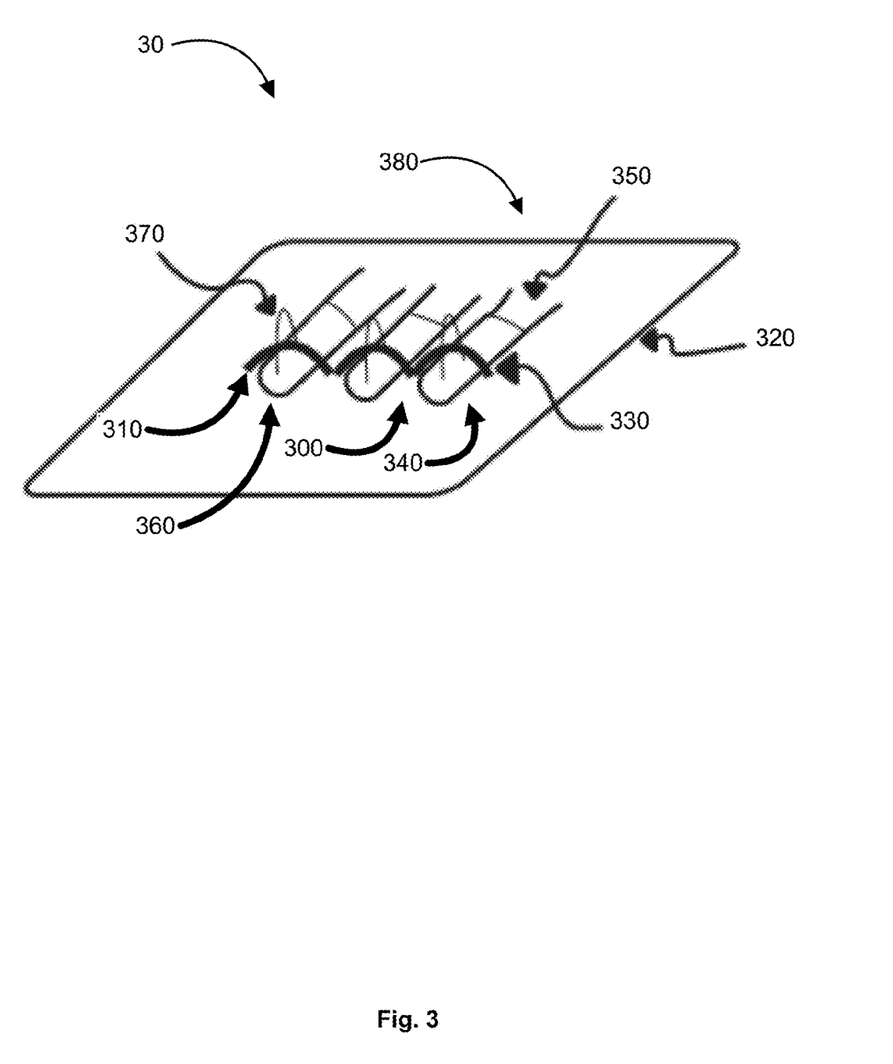
FIG. 3 illustrates a perspective view of an apparatus for therapeutically treating the hand according to an embodiment.

FIG. 3 illustrates a perspective view of an apparatus 30 for therapeutically treating the hand according to an embodiment. The apparatus 30 includes one or more elastic pulleys 300. The pulleys 300 are formed from an elastic cord 310 which can be made out of a flexible and/or stretchable material such as rubber, a rubber band, a bungee cord, a similar material, or combination thereof. The cord 310 is attached to a generally planar surface 320 of a rigid platform 380 at anchor points 330, which forms a gap 340 between adjacent anchor points 330. The gap 340 is generally sized to receive a finger 350. In some embodiments, the cord 310 consists of multiple discrete segments that extend between adjacent anchor points 330 to receive multiple fingers 350.

In operation, a patient inserts one or more fingers 350 in respective gaps 340. The finger(s) 350 are inserted so that the finger pad(s) 360 are exposed while the finger nail(s) (not shown) are adjacent to the surface 320. The patient bends the finger(s) 350 away from the surface 320 generally in a direction 370 (from a proximal to a distal position). As the patient bends the finger(s) 350, the elastic cord 310 provides a positive resistance for exercising and/or strengthening the finger(s) 350. In an aspect, the cord (or cords if it is made of several individual loops) can have a textured and/or heated surface to enhance the therapeutic action of the cords.

In some embodiments, the surface 320 and/or rigid platform 380 is formed of wood, plastic, cardboard, or similar material that is generally inflexible so that the surface 320 and/or rigid platform 380 does not deform during use of the pulleys 300. In some embodiments, the pulleys 300 are formed from two or more elastic cords 310A, 310B, 310N. Each elastic cord 310A, 310B, 310N can have the same or different resistance and can be formed from the same or different materials. The pulleys 300 can be disposed as a component and/or module of a hand therapy kit as described herein. Alternatively, the pulleys 300 can be integrated onto a working surface of a kit, as described above.

Figure 4:
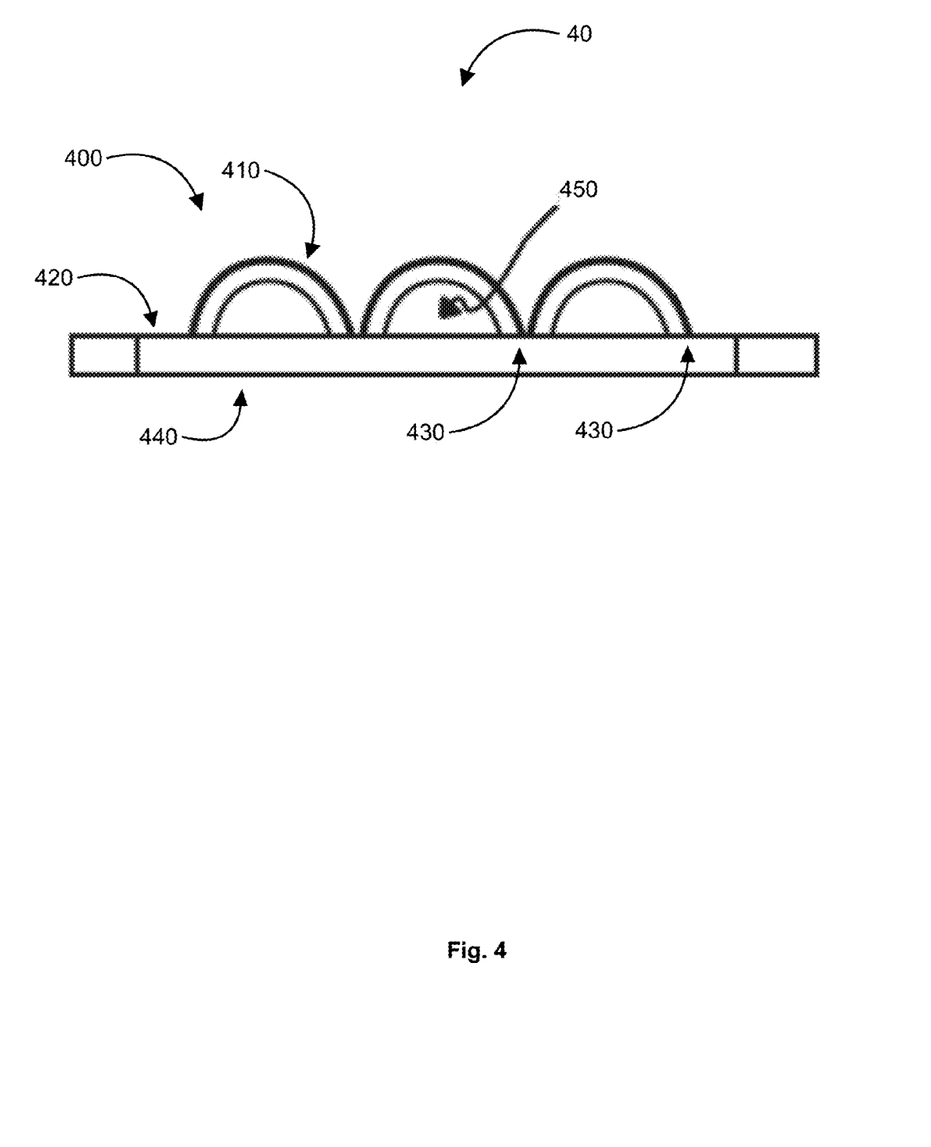
FIG. 4 illustrates a side view of an apparatus for therapeutically treating the hand, which generally corresponds to the apparatus illustrated in FIG. 3.

FIG. 4 illustrates a side view of an apparatus 40, which generally corresponds to the apparatus 30 described above. The apparatus 40 includes one or more elastic pulleys 400 formed of an elastic cord 410, which are secured to a block 440 at anchor points 430. In operation, a user inserts his fingertip(s) 450 under the elastic cord 410, such that the fingertip(s) 450 face towards the cord 410 and away from a surface 420 of the block 440. As discussed above, the surface 420 and the block 440 may be substantially inflexible and can be an independent component of a hand therapy kit or integrated onto a working surface of a kit.

Figure 5:
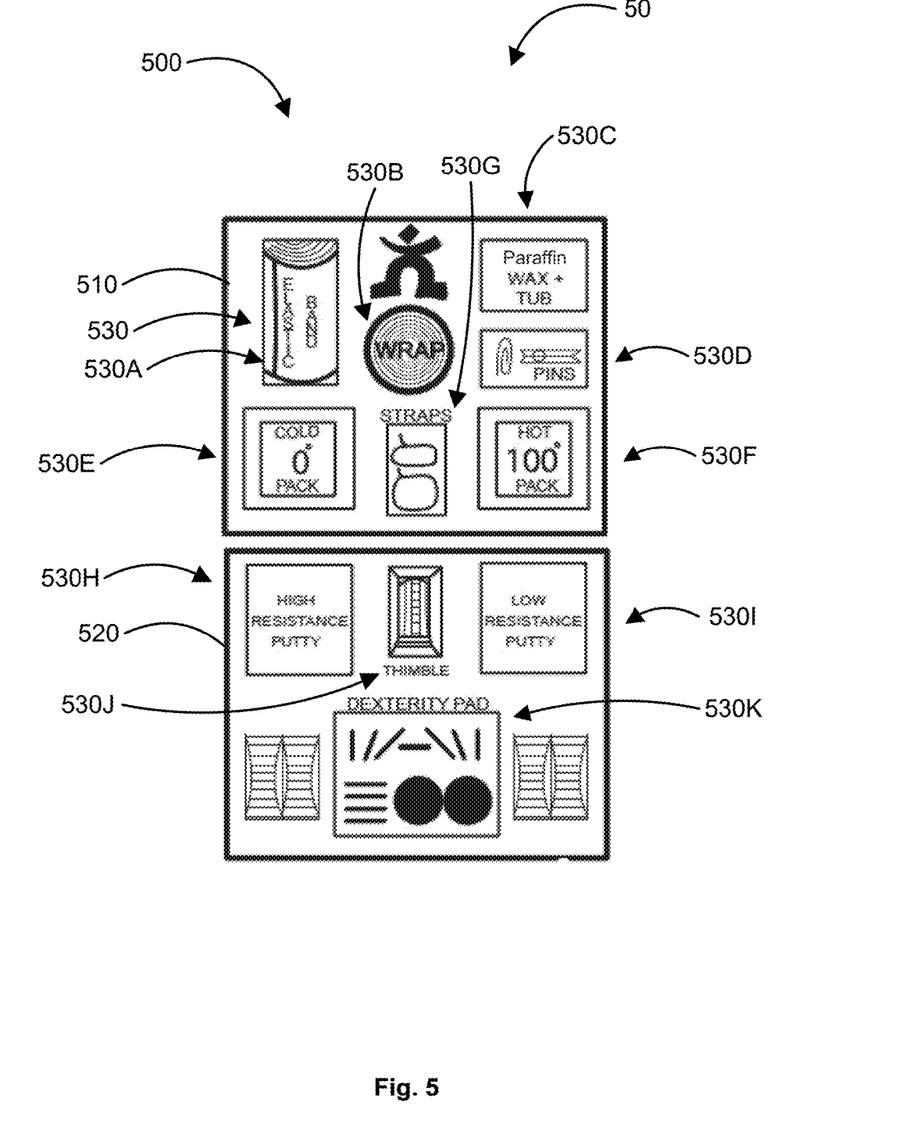
FIG. 5 illustrates a plan view of a kit according to an embodiment.

FIG. 5 illustrates a plan view of a kit 50 according to an embodiment. The kit 50 includes a plurality of modules and components that are integrated into a housing, case or enclosure which is portable, cost-efficient and suited for the present purpose. While the kit may include some elements known in the art, several of the elements described herein are not. In addition, those skilled in the art would appreciate that other elements and modules can be integrated into kit 50 as well.

The kit 50 includes a housing 500 having an upper lid 510 and a lower lid 520 as generally described above. One or more modules 530 for providing home-based therapeutic treatment for the hand are disposed in the kit 50. As illustrated, the modules 530 include an elastic band module 530A, a wrap module 530B, a paraffin wax module 530C, a clothespin module 530D, a cold pack module 530E, a hot pack module 530F, a strap module 530G, a high-resistance putty module 530H, a low-resistance putty module 530I, a thimble module 530J, and a dexterity pad module 530K. Greater or fewer modules 530 can be disposed in the kit 50. In some embodiments, the modules 530 are removable and/or interchangeable.

The elastic band module 530A includes multiple elastic bands having different sizes, shapes, and/or elasticities and can be formed out of rubber (natural or synthetic), bungee cord, or similar material. The elastic band module 530A can be used by a patient to exercise the hand (or various portions of the hand such as one or more fingers, etc.) at different resistances. For example, a patient can place an elastic band over a clenched first for exercising the hand by opening and closing the first against a resistive force provided by the elastic band. Such exercise can increase intrinsic and/or extrinsic muscle strength as well as dexterity. Intrinsic muscles include those that originate and insert within the hand; extrinsic muscles have an origin outside of the hand (e.g., the forearm). The kit 50 and/or elastic band module 530A can include instructions for using the elastic bands. In some embodiments, the elastic bands are color coded by resistivity (e.g., darker-colored bands are more resistive and lighter-colored bands are less resistive).

The wrap module 530B includes an elastic bandage that can be self-adhering in some embodiments. The elastic bandage can be formed out of a stretchable and/or flexible material. In operation, a patient can wrap the elastic bandage around one or more fingers, for example in a distal (towards finger tip) to proximal (towards knuckle) direction, to reduce swelling and/or to guide edema. Such a wrapped elastic bandage can also promote lymphatic drainage. The kit 50 and/or wrap module 530B can include instructions for using the elastic bandage.

The paraffin wax module 530C includes a source of paraffin wax (e.g., a tub) and a bath unit, which includes a heater to heat and melt the paraffin wax. In some embodiments, the bath unit can be designed to heat the paraffin wax to between about 125° F. and about 135° F. In operation, a patient can place her hand (or portion thereof or other extremity) in the bath unit, which contains heated and melted paraffin wax. The heated paraffin wax warms the tissue in the hand/extremity to make it more supple, elastic, and/or flexible before and/or during exercises. Pre-treatment of the hand in the paraffin wax bath can improve pain and range of motion during exercises.

In addition or in the alternative, the paraffin wax module 530C includes a paraffin glove, which can be heated (e.g., in the microwave) and worn by a patient. Such a glove can warm the entire hand at once not only before exercise/therapy but also during exercise/therapy. The kit 50 and/or paraffin wax module 530C can include instructions for using the paraffin wax, bath unit, and/or paraffin glove. In some embodiments, the glove includes a material that is exothermic with stretch to provide warmth during use. The glove can be reusable or microwaveable or washable.

Also, a compression glove could be provided as part of the kit and that can serve to reduce swelling. Such a glove may be a one-size-fits-most and can have an elastic or stretchable material to stretch over hands of various sizes.

The clothespin module 530D includes one or more clothespins and optionally a string, fabric, or other object for attaching clothespins thereto. In operation, a patient uses her fingers to open the clothespins and attach them to the string, fabric, or other object. Such an exercise can improve the strength of the patient's fingers (e.g., the "pinch" strength) as well as her dexterity. The kit 50 and/or clothespin module 530D can include instructions for using the clothespins.

The cold pack module 530E includes one or more cold packs, which can come in a variety of forms such as a flexible cold pack (e.g., containing a gel or beads), a rigid cold pack, etc. The cold pack can be cooled by placing it in a refrigerator or freezer unit. Alternatively, the cold pack can be cooled by inserting ice and/or a cool liquid in an internal cavity defined by the cold pack. In operation, a patient places the cold pack on a body part (e.g., the hand) before or after exercising the body part to reduce swelling and/or reduce pain. The kit 50 and/or cold pack module 530E can include instructions for using the cold packs. The cold pack can be reusable.

The hot pack module 530F includes one or more hot packs, which can come in a variety of forms such as a flexible hot pack (e.g., containing a gel or beads), a rigid hot pack, etc. The hot pack can be warmed by heating it in a microwave or with an electric current. Alternatively, the hot pack can be warmed by pouring a warm liquid (e.g., hot water) into an internal cavity defined by the hot pack. In operation, a patient places the hot pack on a body part (e.g., the hand) before or after exercising the body part to improve flexibility and/or range of motion. The kit 50 and/or hot pack module 530F can include instructions for using the hot packs.

In some embodiments, the cold pack module 530E and the hot pack module 530F are integrated into a single module. For example, the integrated hot/cold pack module can include a thermal pack with a gel that stays hot when heated (e.g., in the microwave) and that stays cool when cooled (e.g., in the freezer). Alternatively, the hot/cold pack module can be a smart material that produces heat when stretched and cools when compressed.

The strap module 530G includes a strap made out of a fabric, such as a nylon or polyester. In operation, a patient can wrap the strap around an object and exercise her hand muscles (e.g., the grip muscles) by pulling on the strap. In some embodiments, the patient can secure the strap in a door jam. In addition or in the alternative, a patient can pull opposing ends of the strap to exercise both hands at the same time. The kit 50 and/or strap module 530G can include instructions for using the straps. In an aspect, a multi-strap finger exercise module allows for exercising of one or more fingers, for example simultaneously. The straps may be elastic or spring loaded from beneath, or may be otherwise mechanically resistive to elongation when under tensile stress. Strength and dexterity of the fingers and of associated hand muscles and tissues is achievable through a regimen of exercise using the elastic strap module 530G.

The high-resistance putty module 530H and low-resistance putty module 530I include various containers or pellets of therapeutic putty having various resistances. The putty can be formed out of silicone, rubber, silicone rubber, or other synthetic and/or natural materials with similar properties. In some embodiments, the resistance of the putty can vary as the user stretches or compresses the putty. In operation, a patient can squeeze the putty in her hand to improve grip and overall hand strength. A patient can also squeeze the putty between her fingers to improve pinch strength and/or to exercise weaker fingers in isolation. A patient can also pull the putty apart using two hands to exercise both hands simultaneously. In some embodiments, the patient can begin physical therapy using the low-resistance putty module 530I and, after gaining strength, the patient can transition to using the high-resistance putty module 530H. The kit 50, the high-resistance putty module 530H, and/or the low-resistance putty module 530I can include instructions for using the putty.

Figure 6:
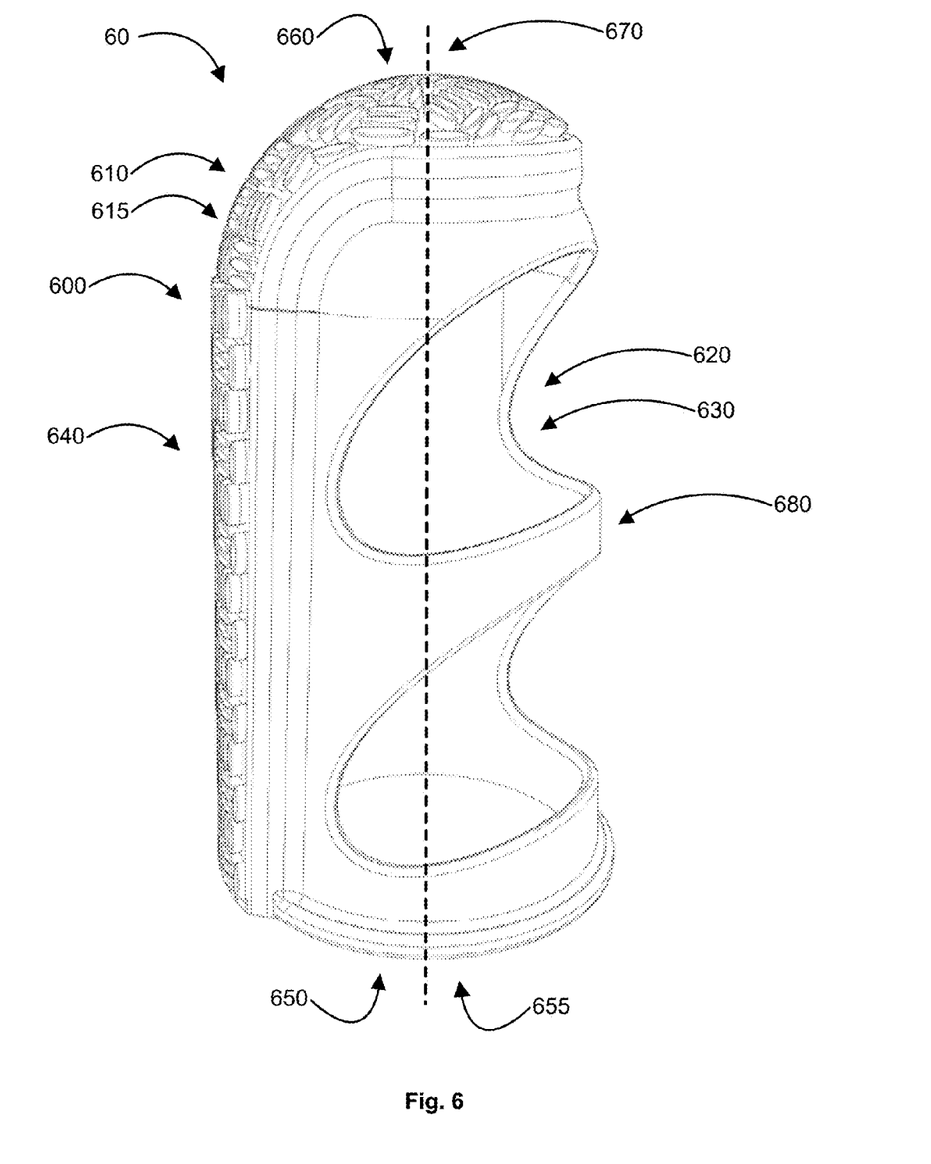
FIG. 6 illustrates a perspective view of a thimble for treating a scar according to an embodiment.

The thimble module 530J includes one or more thimbles for decreasing sensitivity of scars throughout the body and/or for improving fingertip hypersensitivity. FIG. 6 is a perspective view of a thimble 60 that can be included in the thimble module 530J. The thimble 60 has a textured exterior region 610, which can be used for rubbing scar tissue. In addition, the thimble can include an interior cavity 620 lined with silicone. In some embodiments, the thimble module includes one or more thimbles as described in U.S. patent application Ser. No. 14/474,751, entitled "Apparatus for Reducing the Appearance and Effects of Scars," which is hereby incorporated herein by reference and assigned to the same assignee as the present application. A patient can wear the thimble 60 (with the fingertip touching the interior cavity 620) to decrease the sensitivity of a fingertip, which can become hypersensitive due to scarring. In addition, a patient can wear the thimble 60 on a finger to help soften a scar, to improve cosmesis, and/or to decrease pain.

In general, the thimble includes a body 600 having an interior surface 630 and an exterior surface 640. The exterior surface 630 includes features 615 that provide one or more textured regions 610 that a patient can rub against the affected area. The textured regions 610 can have a varying coarseness or roughness. The features 615 can include raised bumps, grooves, or other shapes that have a coarseness appropriate for the skin condition and/or the treatment regimen. The textured regions 610 can have features 615 arranged in various patterns, which can have variations within the pattern such as the distance between each feature and adjacent features, the arrangement of the features (e.g., in linear columns and rows or an offset between adjacent columns and/or rows), and/or the hardness or flexibility of the material that creates the features. These variables, described above, can be the same or different across the textured region 610.

The body 600 has a cavity 620 to receive one or more fingers. A proximal end 650 of the body 600 defines an aperture 655 to allow a finger to penetrate the cavity 620. The interior surface 630 of the distal end 660 of the body 600 is adapted to conform to the tip of one or more fingers. Thus, a patient can mount the apparatus 60 on a finger by inserting the finger(s) through the proximal end 650 of the body 600 and through the cavity 620 to the distal end 660 of the body 600.

The cavity 620 can be cylindrical and can have a central axis 670 extending from the proximal end 650 to the distal end 660 of the body 600. A support member 680 can be disposed on the body 600 to enhance the mechanical strength of the device 60. The support member 680 can be disposed in an orientation orthogonal to the central axis 670.

As discussed above, the thimble device has one or more textured regions 610. For example, a first textured region can have a coarseness appropriate for a first portion of a treatment regimen and a second textured region can have a coarseness appropriate for a second portion of the treatment regimen. The second textured region can have a greater or lower coarseness or roughness than the first textured region. The first and second textured regions can have other variations including the pattern of the features within each textured region, the distance between each feature, the arrangement of the features (e.g., in linear columns and rows or an offset between adjacent columns and/or rows), and/or the hardness or flexibility of the material that creates the features.

In some embodiments, two or more thimbles are included in the thimble module 570J. A first thimble, similar to the thimbles described above, has at least one textured region having a first coarseness appropriate for a first portion of a treatment regimen. A second thimble, also similar to the thimbles described above, has at least one textured region having a second coarseness appropriate for a second portion of the treatment regimen. The thimble module 570J can include additional devices having varying coarseness, which can be used for other portions of the treatment regimen.

Overall, the kit can include contours in its internal walls or working platform structures. For example, outwardly concave contours, hemispherical or similar extrusions can be textured and provide a touching and grasping action for certain therapeutic exercises.

In addition, the thimble module 570J can include a therapeutic cream, which can be used to treat a dermatological condition (e.g., scars, burns, keloids, skin blemishes, incisions, lacerations, abrasions, and/or stretch marks) together or in combination with the thimble described above. The cream can include one, some, or all of the ingredients in Table 1. It is noted that the weight percentages provided in Table 1 are examples and are not intended to be exhaustive. For example, the cream can include plus or minus 1%, 2.5%, 5%, 10%, or 15% of the weight percentage of any ingredient listed in Table 1. The cream can have a pH of about 5.9 (at 25° C.) plus or minus 1%, 2.5%, 5%, 10%, or 15% and it can have a viscosity of about 200,000 cps plus or minus 1%, 2.5%, 5%, 10%, or 15%.

TABLE 1

| Ingredient | Weight Percent | Function |
| --- | --- | --- |
| Deionizied water | 57.30 | Vehicle |
| Glycerine | 5.00 | Humectant |
| Propanediol | 2.00 | Solvent moisturizer |
| SabiWhite ™ (tetrahydrocurcumin 95%) (Sabinsa Corporation) | 0.20 | Skin lightener, antioxidant |
| *Aloe barbedensis* | 2.00 | Anti-inflammatory |
| Carbopol ® Ultrez 10 (carbomer) (Lubrizol Corporation) | 0.80 | Rheology, viscosity |
| Vital ET ™ (disodiumLauriminodipropionate tocopheryl phosphates) (Ashland Inc.) | 2.50 | VE phosphate non-steroidal anti-inflammatory, source of Vitamin E |
| Allantoin | 0.50 | Stimulates new tissue growth, wound healing |
| Muira puama (*ptychopetalum olacoides* bark/root extract (and) glycerin (and) water) | 0.50 | Increase blood flow, antiseptic, antibacterial |
| Cutina ® GMS V (glyceryl stearate) (BASF Corporation) | 1.00 | Emulsifier |
| Phenoxyl T (cetearyl alcohol (and) ceteareth-20) | 2.00 | Emulsifier |
| Alpha-bisabolol | 0.20 | Non-steroidal anti-inflammatory |
| Cocoa butter (*theobroma cacao* seed butter) | 2.00 | Reduces degeneration of skin cells and restores skin flexibility |
| Cremelin ® PURA (vegetable oils) (CREMER OLEO GmbH & Co. KG) | 1.00 | Natural petrolatum |
| Almond oil (*prunus amygdalus dulcis*) | 1.00 | Emollient |
| Olive oil (*olea europaea*) | 1.00 | Soothing, promotes oil spreading and skin smoothness |
| Jojoba oil (*simmondsia chinesis*) | 8.00 | Wax esters for antioxidant, moisture emollient, improves skin elasticity |
| Dow Corning ® 200, 100 cSt (dimethicone) (Dow Corning Corporation) | 0.50 | Silicone spreading |
| Freshcolat ® MGA (menthone glycerine acetal) (Symrise AG) | 1.00 | Skin coolant and refreshant |
| Triethanolamine 99% | 0.60 | pH adjustment |
| Escalol ® 557 Octinoxate (Ashland Inc.) | 1.00 | UV absorber |
| Germaben ® II (propylene glycol (and) diazolidinyl urea (and) methylparaben (and) propylparaben) (Sutton Laboratories) | 1.00 | Preservative |
| Phytotal ™ AI PS (glycerin, aqua, butylene glycol, *euphrasia officinalis* extract, *melissa officinalis* extract, *magnolia biondii* extract, lecithin) (Croda International PLC) | 2.30 | Reduces visible and physical signs of irritation |
| SymSitive ® 1609 (pentylene glycol, 4-t-butylcyclohexanol) (Symrise AG) | 3.00 | Reduces neuropathic pain (e.g., stinging and burning) |
| Cucumber phytobasic in glycerine (*cucumis sativa* extract) | 2.30 | Astringent/skin tightening |
| Pro-Lipo ™ Neo (propanediol (and) lecithin) (Unipex Group Inc.) | 1.30 | Pro-liposome encapsulation skin penetrant; increases skin penetration and bioavailability of entrapped hydrophilic and/or lipophilic active ingredients for better and faster results |

The cream can be infused or stored in a silicone (or similar) elastomer sheet or pad, which can be available in various sizes to use as a dressing over a surgical or traumatic scar. The cream can be located in a recessed compartment within the elastomer sheet or pad. The elastomer sheet or pad can be stored prior to clinical application by using an impermeable or semipermeable peel away covering. For example, the elastomer sheet or pad can be sized and shaped to fit over a caesarian section scar. The sheet or pad can be applied over the entire length of the scar for several weeks following the caesarian section procedure, allowing the scar (and the patient) to benefit from the cream contained in the sheet or pad. Additionally, the sheet or pad can retain moisture, which can soften a scar and protect the skin from post-surgical hypersensitivity.

When used with the thimble, the cream can flow through interstices or channels of the textured regions. For example, the cream can flow through interstices or channels of the first textured region at a first rate and can flow through interstices or channels of the second textured region at a second rate, thereby allowing the cream to flow through the textured regions at the same or different rates.

The kit 50 and/or thimble module 530J can include instructions for using the thimbles.

The dexterity pad module 530K includes different shaped objects and corresponding locations/slots for placing each object. The locations and/or slots are configured to require increasing need for motion, sensibility, strength and/or dexterity, thus training and exercising the patient. In operation, the patient places each object in a corresponding recessed area or slot, which requires fine motor skill, to improve dexterity and function. The development of these skills and strength is generally gradual and utilizes both intrinsic and extrinsic muscles. The kit 50 and/or dexterity pad module 530K can include instructions for using the dexterity pad.

Figure 7:
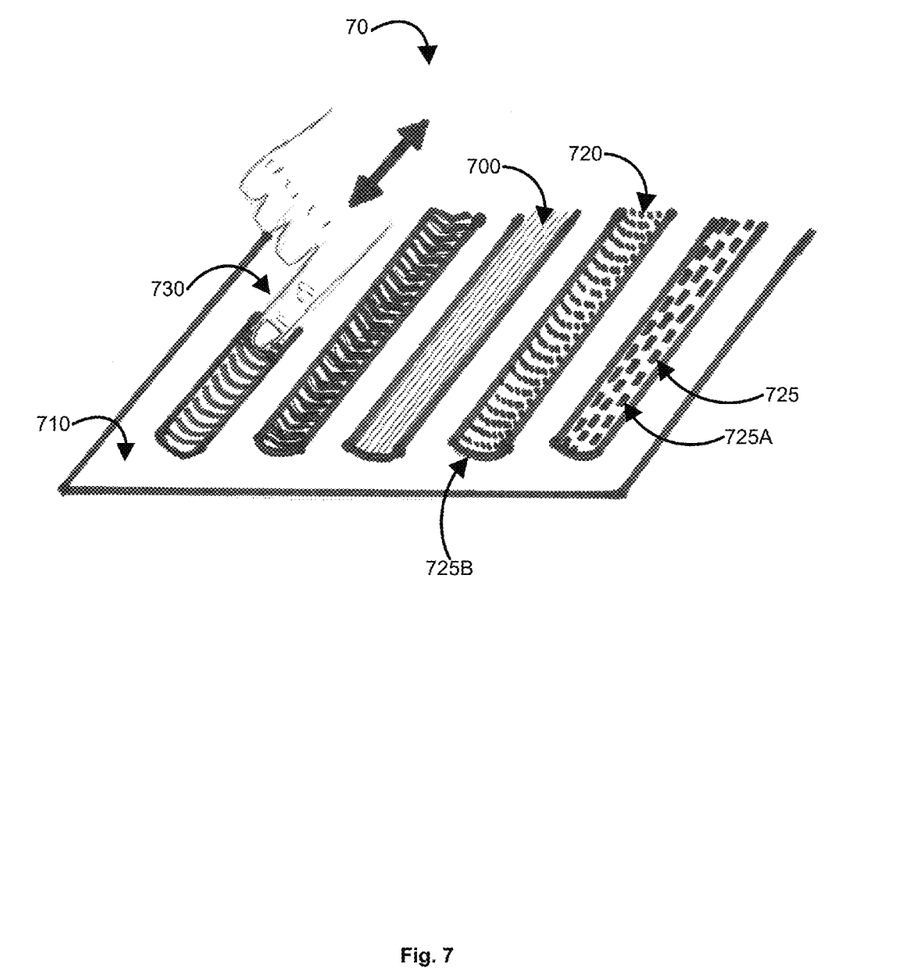
FIG. 7 illustrates a perspective view of a scar revision system.

FIG. 7 illustrates a perspective view of a scar revision module 70 that can be integrated onto the housing of the kit. The scar revision module 70 includes a plurality of elongated channels 700 defined in a surface 710. The channels 700 include one or more textured regions 720 of varying coarseness. The coarseness is defined by features 725 having a respective shape. For example, a feature 725A with a larger shape is coarser than a feature 725B with a smaller shape. The features 725 can be raised or lowered with respect to the surface of each channel 700. In addition, the features 725 can be oriented in the same or different directions, which can define a pattern. The features 725 can also be regularly or irregularly spaced along and/or across the channels 700. In operation, the user can slide a scar tissue on a finger 730 (or other body part) along one or more textured regions 720 to treat the scar (e.g., to reduce sensitivity thereof), similar to the thimble module described above. In some embodiments, the scar revision module 70 is integrated onto a working surface or a lid of the kit.

Therefore, a system, which may be provided in the form of a portable kit, is described for therapy to a patient's fingers and/or hand. The system includes a housing, case or enclosure adapted for and having inclusions and extensions supporting the above-described elements and others. In an aspect, the system is integrated into a briefcase-shaped housing. The housing includes an outer shell body (e.g., plastic, wood, metal). The housing has an inner surface and at least one platform or working surface or platform built therein which supports the plurality of therapy modules described. The inner structure of the housing or case includes one or more flat platforms with recessed modules for various types of therapeutic activity. Also, the system folds onto itself and can be portable (e.g., for carrying while travelling). Therefore, with proper instructions a patient can take the system home (or while travelling) and use it to perform therapy exercises without having to come in to a clinic or facility to actively perform the exercises there. This saves time and money for the patient because he or she does not have to travel, park, check in at a clinic and wait for a practitioner to assist them. Assistance can be in the form of written or verbal instructions or other preparation provided to the patient remotely so the system can be used at home. This is especially important for patients without the means to travel or for the elderly or disabled.

The present invention should not be considered limited to the particular embodiments described above, but rather should be understood to cover all aspects of the invention as fairly set out in the present claims. Various modifications, equivalent processes, as well as numerous structures to which the present invention may be applicable, will be readily apparent to those skilled in the art to which the present invention is directed upon review of the present disclosure. The claims are intended to cover such modifications.

What is claimed is:

1. A hand therapy kit comprising:
a housing that includes a lid, wherein said lid is expandable from a folded configuration to an unfolded configuration to expose a working surface on an inside of said lid;
an elastic cord attached to said working surface, said elastic cord defining a first gap between a first anchor point and a second anchor point on said working surface, said first gap sized to receive a first finger, said elastic cord defining a second gap between a third anchor point and a fourth anchor point on said working surface, said second gap sized to receive a second finger, wherein said elastic cord is configured to provide a first positive resistance as said first finger moves from a first position proximal to said working surface to a second position distal to said working surface and said elastic cord is configured to provide a second positive resistance as said second finger moves from said first position to said second position; and
a plurality of removable hand therapy modules disposed in said housing, said plurality of hand therapy modules including:
a therapeutic elastic band module, said therapeutic elastic band module comprising a plurality of therapeutic elastic bands having different resistances for progressively exercising a hand; and
a wrap module comprising a stretchable fabric adapted to wrap around said first finger to apply a therapeutic pressure thereto.

2. The hand therapy kit of claim 1 further comprising a second elastic cord attached to said working surface, said second elastic cord defining a third gap between a fifth anchor point and a sixth anchor point on said working surface, said third gap sized to receive a third finger, wherein said second elastic cord is configured to provide a third positive resistance as said third finger moves from said first position to said second position.

3. The hand therapy kit of claim 2 wherein said second elastic cord defines a fourth gap between a seventh anchor point and an eighth anchor point on said working surface, said fourth gap sized to receive a fourth finger, wherein said second elastic cord is configured to provide a fourth positive resistance as said fourth finger moves from said first position to said second position.

4. The hand therapy kit of claim 2 further comprising a third elastic cord attached to said working surface, said third elastic cord defining a fourth gap between a seventh anchor point and an eighth anchor point on said working surface, said fourth gap sized to receive a fourth finger, wherein said third elastic cord is configured to provide a fourth positive resistance as said fourth finger moves from said first position to said second position.

5. The hand therapy kit of claim 2 wherein said first elastic cord has a first resistance and said second elastic cord has a second resistance, said first resistance different than said second resistance.

6. The hand therapy kit of claim 4 wherein said first elastic cord has a first resistance, said second elastic cord has a second resistance, and said third elastic cord has a third resistance, said first resistance greater than said second resistance, said second resistance greater than said third resistance.

7. The hand therapy kit of claim 1 wherein said removable hand therapy modules include a paraffin wax module comprising a container of paraffin wax, a heating element, and a bath unit in thermal communication with said heating element.

8. The hand therapy kit of claim 7 wherein said heating element is disposed on said working surface.

9. The hand therapy kit of claim 8 wherein an electric cord of said heating element passes through a sidewall of said housing.

10. The hand therapy kit of claim 7 wherein said removable hand therapy modules include a first putty module comprising a first therapeutic putty having a first resistance.

11. The hand therapy kit of claim 10 wherein said removable hand therapy modules include a second putty module comprising a second therapeutic putty having a second resistance.

12. The hand therapy kit of claim 1 wherein said removable hand therapy modules include a thimble module comprising a thimble having a hollow body with an exterior surface, said exterior surface including a first textured region having a first coarseness and a second textured region having a second coarseness, said first coarseness different than said second coarseness.

13. The hand therapy kit of claim 1 wherein a plurality of elongated channels are defined in said working surface, each channel having a respective coarseness defined by a shape of a feature in said channel.

14. A hand therapy kit comprising:
a housing that includes a lid, wherein said lid is expandable from a folded configuration to an unfolded configuration to expose a working surface on an inside of said lid, wherein a plurality of elongated channels are defined in said working surface, each channel having a respective coarseness defined by a shape of a feature in said channel; and
an elastic cord attached to said working surface, said elastic cord defining a first gap between a first anchor point and a second anchor point on said working surface, said first gap sized to receive a first finger, said elastic cord defining a second gap between a third anchor point and a fourth anchor point on said working surface, said second gap sized to receive a second finger, wherein said elastic cord is configured to provide a first positive resistance as said first finger moves from a first position proximal to said working surface to a second position distal to said working surface and said elastic cord is configured to provide a second positive resistance as said second finger moves from said first position to said second position.

15. The hand therapy kit of claim 14 wherein said removable hand therapy modules include a paraffin wax module comprising a container of paraffin wax, a heating element, and a bath unit in thermal communication with said heating element.

16. The hand therapy kit of claim 15 wherein said heating element is disposed on said working surface.

17. The hand therapy kit of claim 15 wherein said removable hand therapy modules include a first putty module comprising a first therapeutic putty having a first resistance.

18. The hand therapy kit of claim 17 wherein said removable hand therapy modules include a second putty module comprising a second therapeutic putty having a second resistance.

19. The hand therapy kit of claim 14 wherein said removable hand therapy modules include a thimble module comprising a thimble having a hollow body with an exterior surface, said exterior surface including a first textured region having a first coarseness and a second textured region having a second coarseness, said first coarseness different than said second coarseness.

20. A hand therapy kit comprising:
a housing that includes a lid, wherein said lid is expandable from a folded configuration to an unfolded configuration to expose a working surface on an inside of said lid, wherein a plurality of elongated channels are defined in said working surface, each channel having a respective coarseness defined by a shape of a feature in said channel;
an elastic cord attached to said working surface, said elastic cord defining a first gap between a first anchor point and a second anchor point on said working surface, said first gap sized to receive a first finger, said elastic cord defining a second gap between a third anchor point and a fourth anchor point on said working surface, said second gap sized to receive a second finger, wherein said elastic cord is configured to provide a first positive resistance as said first finger moves from a first position proximal to said working surface to a second position distal to said working surface and said elastic cord is configured to provide a second positive resistance as said second finger moves from said first position to said second position; and
a plurality of removable hand therapy modules disposed in said housing, said plurality of hand therapy modules including a therapeutic elastic band module, said therapeutic elastic band module comprising a plurality of therapeutic elastic bands having different resistances for progressively exercising a hand.

21. The hand therapy kit of claim 20, wherein said removable hand therapy modules include a wrap module comprising a stretchable fabric adapted to wrap around said first finger to apply a therapeutic pressure thereto.

22. The hand therapy kit of claim 16 wherein an electric cord of said heating element passes through a sidewall of said housing.

* * * * *